United States Patent [19]
Rector

[11] Patent Number: 5,706,562
[45] Date of Patent: Jan. 13, 1998

[54] FRENUM LOCK

[76] Inventor: Charles W. Rector, 3304 Russel Rd., Cenralia, Wash. 98531

[21] Appl. No.: 745,742

[22] Filed: Nov. 12, 1996

[51] Int. Cl.⁶ ..................................................... A01N 1/00
[52] U.S. Cl. ....................................................... 27/21.1
[58] Field of Search ................................. 27/21.1, 25.1

[56] References Cited

U.S. PATENT DOCUMENTS

| | | | |
|---|---|---|---|
| 2,142,614 | 1/1939 | Mitchell | 27/21.1 |
| 3,103,052 | 9/1963 | Rector | 27/21.1 |
| 3,195,215 | 7/1965 | Rector | 27/21.1 |
| 3,205,553 | 9/1965 | Pfeifer | 27/21.1 |
| 3,421,190 | 1/1969 | Rector | 27/21.1 |
| 3,507,017 | 4/1970 | Rector | 27/21.1 |
| 3,584,620 | 6/1971 | Hale | 27/21.1 |
| 4,240,186 | 12/1980 | Rector | 27/21.1 |

FOREIGN PATENT DOCUMENTS 741953  9/1966  Canada.

*Primary Examiner*—Kien T. Nguyen
*Attorney, Agent, or Firm*—Thomas W. Secrest

[57] ABSTRACT

This invention is directed to a frenum lock, also know as a natural expression former, for use by morticians. The improvement of this invention is the increased thickness of the central area or the medial area of the frenum lock and the decreased thickness of the peripheral areas, i.e., spaced end or wing area, of the frenum lock. As a result, there is more rigidity in the medial area of the subject frenum lock and more flexibility in the peripheral areas or wing ends of the frenum lock. This makes it easier for the mortician to insert and to position the frenum lock between the lips and the gums of the cadaver for the cadaver to have a natural appearance.

23 Claims, 2 Drawing Sheets

FRENUM LOCK

CROSS-REFERENCES TO RELATED PATENT APPLICATIONS (if any)

There is no related pending application.

STATEMENT AS TO RIGHTS TO INVENTIONS MADE UNDER FEDERALLY SPONSORED RESEARCH AND DEVELOPMENT (if any)

This subject invention was made with private finances and there was no federally sponsored research and development.

BACKGROUND OF THE INVENTION

My three U.S. Pat. Nos. 3,103,052; 3,195,215; and 4,240,186 disclose a natural expression former. This invention is an improvement on the invention of these three enumerated patents.

1. Field of the Invention

This invention makes it easier to use, to insert, and to position the expression former into the mouth of a corpse or a cadaver. The central area or medial area of the expression former is formed so as to have a greater thickness than the peripheral areas or wing ends. This allows increased cusp curvature of the frenum lock. There is a taper in thickness at the medial area from about 0.011 inches to 0.013 inches to a peripheral area having a thickness in the range of about 0.007 inches to about 0.009 inches with accompanying thinness and flexibility of the frenum lock. There is increased rigidity and strength at the medial area and increased flexibility at the peripheral areas or wing ends. The thin and flexible wing ends permit wider spreading of the expression forming wing-like portions of the frenum lock upon insertion of the frenum lock into the mouth of the corpse or the cadaver and also permit greater adaptation of the former to the dental arch of the corpse or cadaver.

The rigid medial area and the flexible peripheral areas make it easier to work the expression former into the mouth of the cadaver and also make it possible for the cadaver to have a more natural appearance around the mouth and the lips.

2. Description of the Prior Art

On 1963 Sep. 10, there was issued to the applicant U.S. Pat. No. 3,103,052 for a natural expression former which could be easily manipulated and trimmed to the proper size for the mouth of the cadaver.

On 1965 Jul. 20, there was issued to the applicant U.S. Pat. No. 3,195,215 directed to a natural expression former with bite indentation.

On 1980 Dec. 23 there was issued to the applicant U.S. Pat. No. 4,240,186 for a frenum lock having the improvement of positioning the dividing lines and the medial area of the natural expression former or frenum lock to permit wider spreading of the expression forming wing ends on insertion of the expression former into the mouth of the corpse or cadaver and to permit greater adaptation of the expression former to the dental arch of the corpse or cadaver.

There is a Canadian patent number 741,953, entitled NATURAL EXPRESSION FORMER date of 1966 Sep. 6 corresponding to U.S. Pat. No. 3,103,052.

SUMMARY OF THE INVENTION

This invention is directed to an improved frenum lock. The improvement comprises a thicker central area or medial area of the frenum lock so as to have more firmness at the central area. Also, the improvement comprises thinner peripheral areas to have more flexibility at the peripheral areas of the frenum lock.

As a result, it is easier to manipulate the frenum lock between the lips and gums of the cadaver and to impart to the cadaver a more natural and pleasing appearance.

OBJECTS AND ADVANTAGES

One of the objects and advantages of this invention is to provide a frenum lock having a thicker central area and thinner peripheral areas than prior frenum locks;

Another object and advantage is to provide a frenum lock with a more rigid central area and more flexible peripheral areas than prior frenum locks;

Another object and advantage is to provide a frenum lock which is easier to work with respect to the lips and the gums of the cadaver; and Additional objects, advantages and novel features of the invention will be set forth in part in the description which follows, and in part will become apparent to those skilled in the art upon examination of the following or may be learned by the practice of the invention. The objects and advantages of the invention may be realized and attained by means of the instrumentalities and combinations particularly pointed out in the appended claims.

DESCRIPTION OF THE PREFERRED EMBODIMENT(S)

Figure 1:
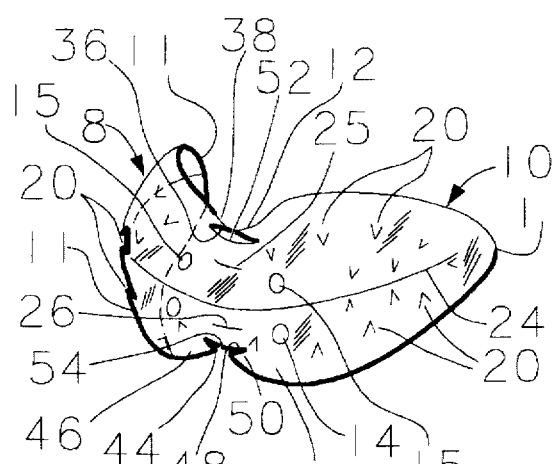
FIG. 1 is a perspective view of a natural expression former or frenum lock embodying the improvement of this invention, a thicker and more rigid central area, and thinner and more flexible peripheral area than prior frenum locks.

The frenum lock or natural expression former of this invention comprises many of the characteristics of the expression former of my three U.S. Pat. Nos. 3,103,052; 3,195,215; and 4,240,186. Reference will be made to these three United States patents both directly and indirectly.

The frenum lock 8 or natural expression former 8 of this invention comprises a precontoured plate 10 having a pair of peripheral areas 11 or wing ends 11 and a central area 12 or a medial area 12. The wing ends 11 have a thickness in the range of 0.007 inches to 0.009 inches for increased flexibility. The medial area 12 has a thickness in the range of 0.011 inches to 0.013 inches for rigidity. Although termed a plate 10, it is not flat, but is generally curved transversely to fit the dental arch. Also, it is curved at right angles to the transverse curvature substantially throughout, thereby having an inherent double curvature which renders it form-sustaining. The material of the plate 10 is normally substantially inelastic and is characteristically resilient so that it retains its inherent double curvature and tends always to return to its precontoured shape. Yet the material of the plate is flexible to permit fitting the frenum lock 8 to almost any mouth without necessity of altering the frenum lock 8. A series of sharp spurs 20 are raised from the plate 10 in strategic positions to engage and hold the musculature around the mouth.

Figure 3:
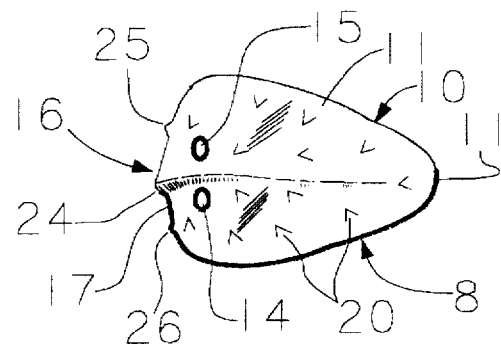
FIG. 3 is a transverse sectional view taken through the mid-line of the frenum lock, which for clarity of illustration, is shown with somewhat exaggerated thickness.

In this case, the wing ends 11 are of generally no greater curvature than the medial area 12. The wing ends 11 curve less transversely, particularly toward the more or less tapered ends 11a than the medial area 12. The bite indentation comprises a transverse ridge 24 formed in congruity with the double curvature of the plate 10 by the forward offset of the upper portion 16 of the plate from the lower portion 17. Since the upper portion 16 may at times be used as the lower portion, as will shortly be explained, it will be convenient to refer to the portion 16 as the upper portion 16, whichever way the former is employed. Both the upper and lower portions 16 and 17 still possess double curvature. The curvature of one portion merely continuing that of the other portion after the offset illustrated as in the sectional view of FIG. 3. The transverse ridge 24 formed by such offset is smooth vertically, blending into the upper and lower portions 16 and 17. The ridge 24 extends transversely, at least across the medial area 12 and, preferably, as is illustrated, extends well around the sides of the former into the wing ends 11. The transverse ridge 24 gradually decreases in size, always blending into the double curvature, and finally fading into the reduced inherent curvature near the ends of the wing ends 11.

Figure 4:
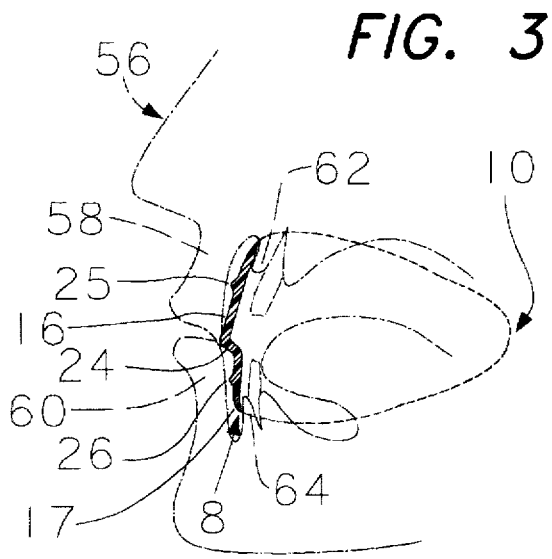
FIG. 4 is a sectional view of the frontal portion, only, of the expression former, with the outline of the entire expression former shown by dotted lines, as inserted in the mouth of a corpse having a natural overbite.
Figure 5:
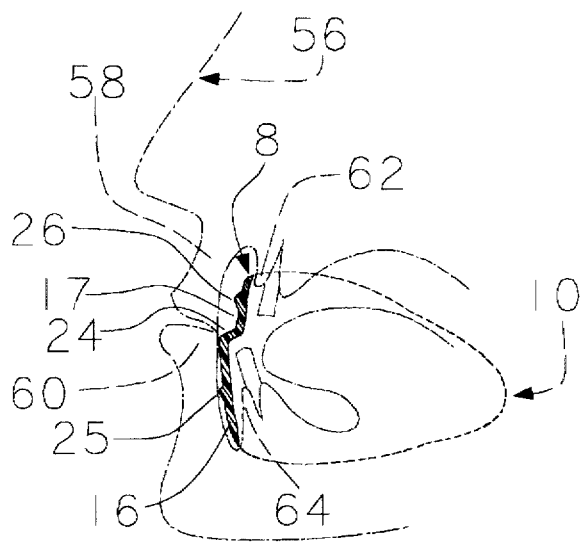
FIG. 5. is a sectional view of the frontal portion, only, of the expression former, with the outline of the entire expression former shown by dotted lines, as inserted in the mouth of a corpse having a natural underbite.

This precontoured transverse ridge 24 serves many purposes and constitutes a marked improvement in expression formers. First, it serves as a bite indentation for accommodation of overbite or underbite, as illustrated in FIGS. 4 and 5 respectively. Actually, very few persons have incisors which occlude perfectly when the lower jaw is in a relaxed position, and usually there is some degree of overbite as illustrated in phantom line of the teeth in FIG. 4. Nonocclusion in the reverse direction (underbite), see FIG. 5, is more rare, yet not infrequent. The transverse ridge 24 or bite indentation preformed into the instant natural expression former 8 is designed to fit either type of mouth more closely and naturally than prior art frenum lock. Since overbite is much more common, the frenum lock 8 will normally be used in the manner shown in FIG. 4, where the lower jaw is slightly offset to the rear of the upper jaw. The expression former 8 of this invention is normally constructed with only a moderate amount of offset so as to form a ridge 24 which is not large in proportion to the overall size of the expression former. It is to be recognized that expression formers may be manufactured with larger amounts of bite indentation to accommodate extreme cases of overbite or underbite. However, the flexibility of the illustrated expression former of this invention permits adapting the same to most mouths.

A related purpose of the preformed bite indentation is to provide a guide for normal relative positioning of the incisors so as to give the jaws a more relaxed appearance to the face. Because of its improved form and inherent strength, the expression former 8 is capable of serving, in conjunction with the injection needles and accompanying wire, as a stabilizer for the lower jaw. The medial connecting area 12 is of a more rigid and thicker construction than prior expression formers. This construction assists in stabilizing the lower jaw. While the wire serves to support the lower jaw, the expression former 8 itself is needed to aid in the normally slightly rearward positioning thereof with respect to the upper jaw. When fitted into position as shown in FIG. 4, the bite indentation holds the incisors and therefore the jaws in optimum relative position for a normal facial expression. In the case of underbite, the expression former 8 serves the same purpose when inverted, as illustrated in FIG. 5. Further, the thin wing ends 11 are more flexible and yieldable to the configuration of the lips than prior expression formers. The result is a more natural expression in the lip area of the cadaver.

After the expression former 8 has been positioned between the lips and the gums, an injector needle 30 may be inserted in the front part of the upper jaw. An injector needle 30 may be inserted into the front part of the lower jaw. Then a wire 32 may be attached to the two injector needles 30 and twisted to draw together the lower jaw and the upper jaw. This positions the jaws of the cadaver.

Figure 2:
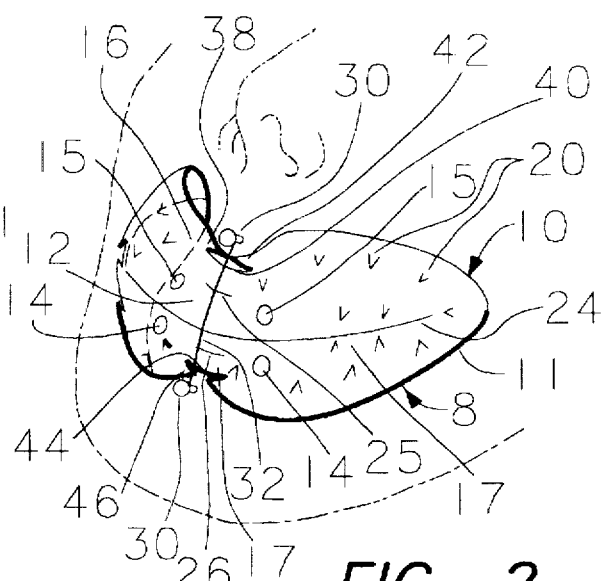
FIG. 2 is a perspective view of the improved expression former shown in relation to the features of a corpse and showing its relationship to injector needles and wires normally used with the expression former or frenum lock.

After installation with injector needles 30, the end of the accompanying twisted wire 32, as illustrated in FIG. 2, is twisted and its looped end is inserted into one of the laterally spaced apertures 14 provided for this purpose in the rearwardly offset lower portion 17. Apertures 15 are also provided in the upper portion 16 to increase ventilation and these may be used in the same manner as apertures 14 to receive the end of the twisted wire 32. This is a convenient way to eliminate bulging of the lips caused by the end of the twisted wire 32. The end of the twisted wire 32 is tucked away in an aperture 14 or 15 in the expression former 8.

While the bite indentation serves as a positioner and stabilizer for the lower jaw, the incisors positioned therein tend to stabilize the expression former 8 itself by engagement with the transverse ridge 24. This accomplishes another purpose of the bite indentation, which is to render the expression former 8 more stable in the mouth during the trial and error positioning of the musculature to form a natural expression. It operates in this manner whether the former is being used in a mouth having a characteristic overbite as in FIG. 4 or a characteristic underbite as in FIG. 5. The increased thickness of the medial connecting area 12 is also of value as the expression former 8 is more stable than prior art expression former.

A further advantage of the bite indentation is the fact that it imparts greater strength to the expression former. It will be observed that the ridge 24 extends substantially forwardly and generally in the plane of transverse curvature of the expression former. The ridge is the largest in the medial connecting area 12 of the expression former 8. The ridge decreases in size toward the wing ends 11. The wing ends blend into the vertical curvature of the expression former 8 thereby imparting a degree of double curvature of their own to the plate 10, supplementing the coexisting double curvature of the plate 10. Also, it can be seen, particularly in FIG. 3, that the curvature vertically of the upper portion 16 is offset not only forwardly of the lower portion 17 because of the ridge 24, but also at a slight angle thereto. The collective effect of the rounded edge or the ridge 24 and the displaced and angularly offset curvatures of the upper and lower portions 16 and 17 is to impart a greater degree of strength to the expression former 8 than would be the case if the ridge 24 were not present. The same effect could be achieved without a ridge by an increased double curvature in the medial area 12, but a natural appearance of the mouth would not be obtained. The result is that the subject expression former 8 is stronger, yet flexible and a more adaptable expression former 8 which provides a closer fit with the teeth and becomes less likely to be noticed by an observer. The increased strength and thickness of the medial connecting area 12 of the plate 10 also provides a more firm base for support of the musculature around the central portion of the mouth as it is engaged with the spurs 20.

With the subject expression former 8, the wing ends 11 are of thinner material and more flexible than prior expression formers. As a result, the spurs 20 are thinner and sharper than the spurs in prior expression formers. The spurs 20 may therefore be made smaller than heretofore possible to avoid excessive mutilation of the tissues during adjustment of the facial expression.

Another very important advantage of the preformed bite indentation is its usability in an edentulous mouth, i.e. as a "denture replacer." In the absence of teeth or dentures, the preformed offset of upper and lower portions 16 and 17 simulate the natural offset more closely than would a smoothly curved expression former not having such an offset. To enhance its use as a denture replacer, another feature is included in the expression former 8, namely the closure guide lines 25 and 26. In the illustrated case, these are horizontal raised lines impressed in the upper and lower portions 16 and 17, respectively, of the plate 10 during manufacture. Since the plate 10 is preferably transparent, markings may be formed in or marked on the plate 10 by means other than impression to provide approximate guides for closure of the jaws during installation. For this purpose, the guide lines are normally spaced about three-fourths of an inch apart and about equally above and below the bite indentation ridge 24 as guides for positioning the gums with respect to the ridge 24. Such guide lines assist the operator when teeth or dentures are present, as well as in their absence.

Figure 6:
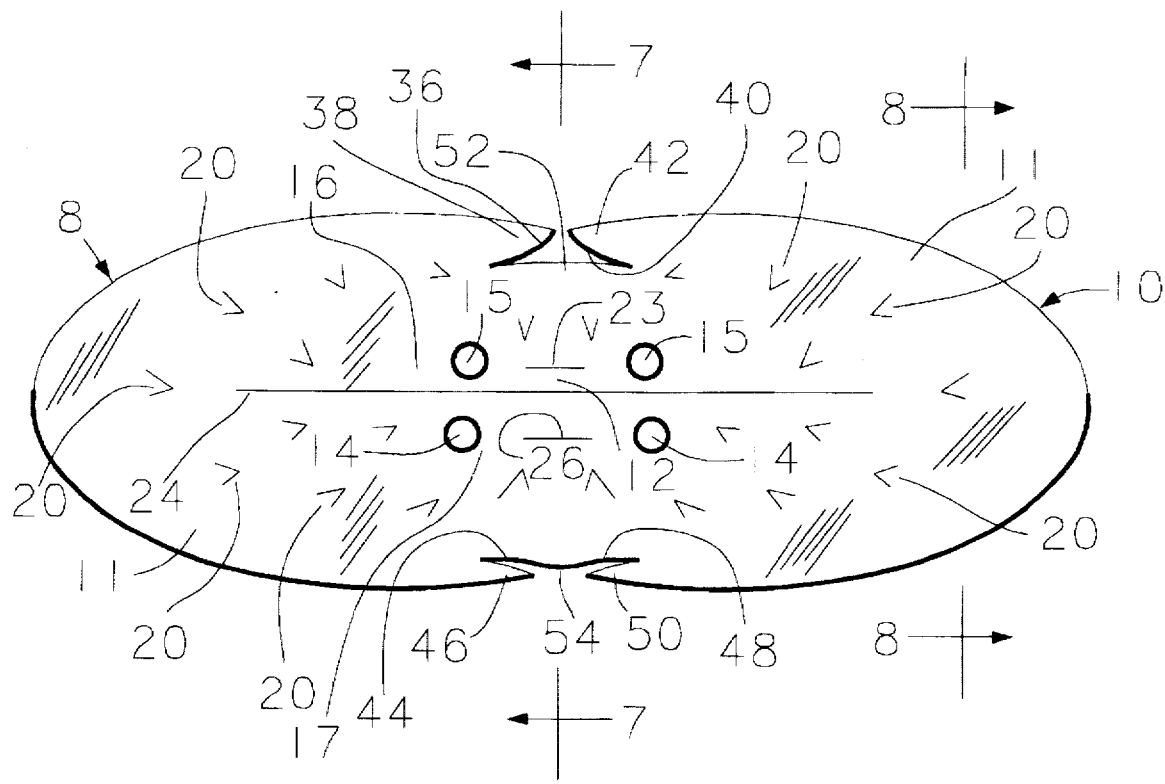
FIG. 6 is a front elevational view of the frenum lock or expression former, drawn to, approximate, exact scale.
Figures 7, 8:
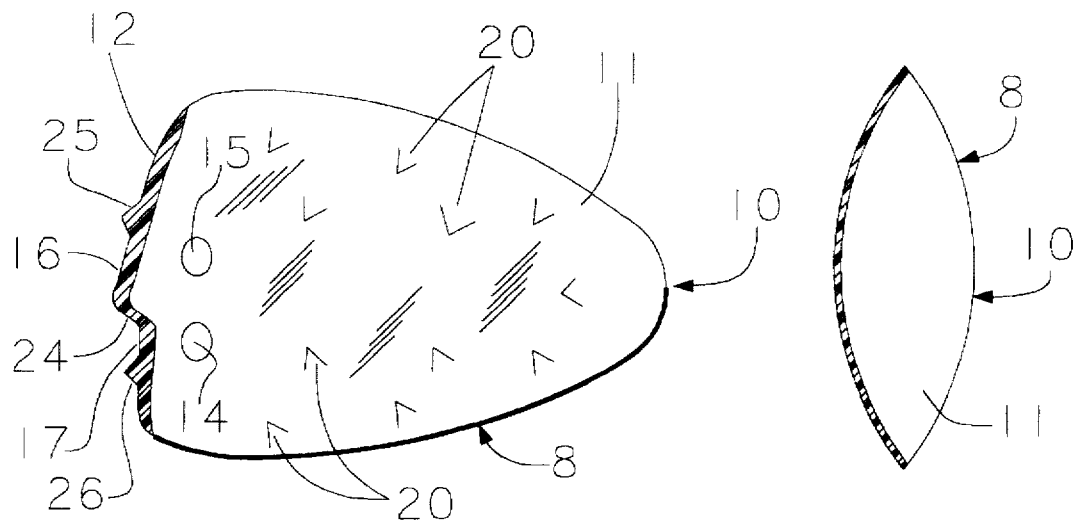
FIG. 7 is a vertical cross-sectional view taken on line 7—7 of FIG. 6 illustrating the thicker and more rigid central areas of the expression former.
FIG. 8 is a cross-sectional view taken on line 8—8 of FIG. 6 and illustrates the thinner and more flexible peripheral areas of the expression former.

In the drawings, it is seen that in the medial area 12 that in the upper left part, see FIGS. 1, 2, and 6, there is a first dividing line 36 which forms a first flap 38. Then, in the upper medial area 12 and on the right there is a second dividing line 40 and a second flap 42.

In the lower part of the medial area 12 and on the left there is a third dividing line 44 which forms a third flap 46. Then, on the lower medial area 12 and on the right there is a fourth dividing line 48 which forms a fourth flap 50.

At the junction of the dividing lines 36 and 40 there may be considered to be a point edge 52. Likewise, at the junctions of the dividing line 44 and dividing line 48 there may be considered to be a point edge 54.

It is seen that each of the flaps 38, 42, 46, and 50 are distinct and separate from the expression former and that the inner part of each of the flaps connects with an adjacent wing ends 11.

The expression former 8 can be prepared from a blank plastic and then formed into the desired configuration. The dividing lines can be manually cut or can be formed in the forming of the expression former.

I consider that the dividing lines and the flaps make it easier to work the expression former 8 into the mouth of the corpse or cadaver. The expression former 8 can be placed between the lips and the gums of the corpse or cadaver. The expression former 8 permits a wider spreading of the expression wing ends 11 on insertion of the expression former 8 into the mouth of the corpse or cadaver and also permits greater adaptation of the expression former 8 to the dental arch of the corpse.

The expression former 8 or frenum lock 8 is of a size and marginal shape to fit between the lips and cheeks and the gums and teeth of the corpse and to extend beyond the lips. Indeed, it extends materially beyond the orbicularis oris which encircles and to a degree controls the expression of the lips. The expression of the lips is not wholly controlled by the orbicularis oris muscle but is also controlled to an appreciable extent by muscles which radiate from the orbicularis oris. In order to restore a natural expression to the mouth it is necessary that the natural tension of each of these muscles be substantially restored, and especially those adjacent the corners of the mouth.

To accomplish this, the expression former 8 is provided with a series of spurs 20 surrounding the lips and in general directed towards the lip margins. These spurs 20 are preferably arranged in two series. Each series is generally oval in shape and are in each expression former 8 including the wing ends 11. For example, the spurs 20 are arranged in an oval close to the lip margins and also are arranged in an outer oval. The spurs 20 close to the lip margin are intended to pierce and to engage the orbicularis oris muscle and thereby retain the lips closed and the expression of the cadaver in a normal expression. The outer oval of the spurs 20 engage primarily the radial musculature and prevent these muscles from sagging, thereby restoring the normal tension and the expression to them and to the face of the cadaver as a whole.

It is not sufficient to maintain the lips closed but the jaws must also be held closed. To accomplish holding the jaws closed there are used injector needles 30 and accompanying twisted wire 32 as illustrated and previously discussed.

In use, the expression former 8 or frenum lock 8 is inserted between the gums and the teeth and the lips. After the jaws have been closed properly and held, the expression former 8 is engaged by the spurs 20 with the muscles surrounding the lips. Care is taken to restore the initial tension to the muscles so as to produce a natural expression in the corpse. Disengagement and reengagement with the muscles to achieve the desired result by trial and error is easily accomplished. If the plate 10 is of a curvature greater than the dental arch of the corpse it may be flexed in the medial area 12. This is especially so in view of the dividing lines and wing ends 11. The expression former 8, without distortion or change in the shape of the wing ends 11 and without buckling at the relatively flat medial connecting area 12, can be flexed. Similarly, if the dental arch is of insufficiently great curvature the frenum lock 8 may be bent outwardly to fit, without buckling, in the medial connecting area 12, and without substantial distortion at any place of the frenum lock 8 and also the lips of the cadaver.

The frenum lock 8 or expression former 8 may be formed of a suitable plastic such as polyvinyl chloride, polyethylene, methyl methacrylate, polypropylene and the like. The plastic should be a thermal plastic so that it can be readily formed under heat to the desired curvature. Again, the expression former 8 may be formed from a blank piece of material and then under heat and pressure formed to the desired curvature. The spurs 20 may be formed by a suitable die as well as the apertures or passageways 14 and 15. Likewise, the dividing lines 36, 40, 44, and 48 may be formed by suitable dies or may be formed manually.

The expression former 8 has a threefold purpose: to close the lips, to form the mouth, and to replace the dentures. In addition, it cooperates with jaw-closing devices commonly used in preparing a cadaver for burial. The spurs 20 are strategically located to support the general buccal musculature, and to facilitate forming the overall desired facial expression. Each spur 20 is located to control a particular muscle. The inner spurs 20 regulate the orbicularis oris as a whole and support the lips in a proper position. The wing ends 11 or cups 11 are precurved and maintain their curvature to the contour of the gums and teeth in the vertical direction as well as in the transverse direction.

In preparing this patent application, I did not make a patent search. However, to repeat, I have three existing patents directed to a natural expression former, U.S. Pat. Nos. 3,103,052; 3,195,215; and 4,240,186. I consider that this invention defines over each of the inventions in the aforementioned patents as in this invention there is recited a thicker and more rigid medial connecting area 12 having a thickness in the range of 0.011 inches to 0.013 inches, and a flexible wing ends 11 having a thickness in the range of 0.007 inches to 0.009 inches for a person preparing a cadaver for burial to more easily insert the expression former 8 into the mouth of the cadaver in between the mouth and the gums, so as to permit wider spreading of the expression forming wing ends 11 on insertion of the expression former 8 into the mouth of the corpse, and also permits a greater adaptation of the expression former 8 to the dental arch of the cadaver. The thicker medial connecting area 12 as compared to the prior art imparts rigidity to the expression former 8 in the dental arch of the cadaver. The thinner wing ends 11 as compared to the prior art allow more flexibility of the expression former 8 in the peripheral areas so as to be more accommodating to the lips of the cadaver.

An improvement in an expression former for insertion between the lips and the teeth and gums of a corpse, comprising a thin plate of resilient, limitedly flexible, yet substantially inelastic material, having an inherent form-sustaining double curvature overall to fit the curvature of the dental arch, said plate further having a marginal shape defining a pair of wing ends and a medial connecting area, and a size and shape to extend along the gums beyond the lips at all points, spurs on said plate for engagement with the mouth musculature, an upper portion offset forwardly of a lower portion thereof at least in the medial area, and a substantially continuous wall connecting said offset portions thereof at least in the medial area, to define a transverse bite indentation ridge therebetween extending along the line of nonocclusion of the forward teeth; and wherein said improvement comprises the medial connecting area being thicker than the wing ends for greater rigidity in the medial connecting area and for greater flexibility in the wing ends; the thickness of the medial connecting area being in the range of 0.011 inches to 0.013 inches; and the thickness of wing ends being in the range of 0.007 inches to 0.009 inches.

An improvement in an expression former for insertion between the lips and the teeth and gums of a corpse, comprising a thin plate of resilient, limitedly flexible, yet substantially inelastic material, having an inherent form-sustaining double curvature overall to fit the curvature of the dental arch, said plate further having a marginal shape defining a pair of wing ends and a medial connecting area, and a size and shape to extend along the gums beyond the lips at all points, spurs on said plate for engagement with the mouth musculature, an upper portion offset forwardly of a lower portion thereof at least in the medial area, and a substantially continuous wall connecting said offset portions thereof at least in the medial area, to define a transverse bite indentation ridge therebetween extending along the line of nonocclusion of the forward teeth; and wherein said improvement comprises in said medial connecting area a first dividing line and a second dividing line; said first dividing line being in the direction of an adjacent wing end and defining a first flap whose free end is distinct and separate from the medial connecting area; said second dividing line being in the direction of an adjacent wing end and defining a second flap whose free end is distinct and separate from the medial connecting area; the inner part of the first flap connecting with an adjacent wing end; the inner part of the second flap connecting with an adjacent wing end; and said first dividing line and said first flap and said second dividing line and said second flap permitting wider spreading of the expression forming wing ends on insertion into the mouth of the corpse and permitting greater adaptation to the dental arch of the corpse.

An improvement in an expression former for insertion between the lips and the teeth and gums of a corpse, comprising a thin plate of resilient, limitedly flexible, yet substantially inelastic material, having an inherent form-sustaining double curvature overall to fit the curvature of the dental arch, said plate further having a marginal shape defining a pair of wing ends and a medial connecting area, and a size and shape to extend along the gums beyond the lips at all points, spurs on said plate for engagement with the mouth musculature, an upper portion offset forwardly of a lower portion thereof at least in the medial area, and a substantially continuous wall connecting said offset portions thereof at least in the medial area, to define a transverse bite indentation ridge therebetween extending along the line of nonocclusion of the forward teeth; and wherein said improvement comprises the expression former defined in claim 1 wherein the plate is of transparent plastic material and further includes jaw closure guide markings on the medial section of said plate spaced above and below said ridge at distances indicating optimum jaw closure; the expression former defined in claim 1 wherein the plate is of transparent plastic material and further includes jaw closure guide markings on the medial area of said plate spaced above and below said ridge at distances indicating optimum jaw closure.

An improvement in an expression former for insertion in the mouth of a corpse, comprising a thin, flexible plate having spurs thereon for engagement with the mouth musculature, and further having transversely spaced end portions to extend beyond the corners of the mouth and a frontal section connecting said end portions, said plate being of substantially form-retentive material and having an inherent curvature at least transversely of the mouth to fit the curvature of the dental arch, said plate further having upper and lower portions of the shape and size to extend beyond the teeth between the gums and the lips, the upper portion being offset forwardly of the lower portion, and a connecting ridge between said upper and lower portions and extending transversely of the plate at least across said frontal section, said offset and ridge forming a bite indentation to accommodate nonocclusion of at least the forward teeth; wherein said improvement comprises the medial connecting area being thicker than the wing ends for greater rigidity in the medial connecting area and for greater flexibility in the wing ends; the thickness of the medial connecting area being in the range of 0.011 inches to 0.013 inches; and the thickness of wing ends being in the range of 0.007 inches to 0.009 inches.

An improvement in an expression former for insertion in the mouth of a corpse, comprising a thin, flexible plate having spurs thereon for engagement with the mouth musculature, and further having transversely spaced end portions to extend beyond the corners of the mouth and a frontal section connecting said end portions, said plate being of substantially form-retentive material and having an inherent curvature at least transversely of the mouth to fit the curvature of the dental arch, said plate further having upper and lower portions of the shape and size to extend beyond the teeth between the gums and the lips, the upper portion being offset forwardly of the lower portion, and a connecting ridge between said upper and lower portions and extending transversely of the plate at least across said frontal section, said offset and ridge forming a bite indentation to accommodate nonocclusion of at least the forward teeth; wherein said improvement comprises in said frontal section a first dividing line and a second dividing line; said first dividing line being in the direction of an adjacent end portion and defining a first flap whose free end is distinct and separate from the frontal section; said second dividing line being in the direction of an adjacent end portion and defining a second flap whose free end is distinct and separate from the frontal section; the inner part of the first flap connecting with an adjacent end portion; the inner part of the second flap connecting with an adjacent end portion; and said first dividing line and said first flap and said second dividing line and said second flap permitting wider spreading of the expression forming end portions on insertion into the mouth of the corpse and permitting greater adaptation to the dental arch of the corpse.

An improvement in an expression former for insertion in the mouth of a corpse, comprising a thin, flexible plate having spurs thereon for engagement with the mouth musculature, and further having transversely spaced end portions to extend beyond the corners of the mouth and a frontal section connecting said end portions, said plate being of substantially form-retentive material and having an inherent curvature at least transversely of the mouth to fit the curvature of the dental arch, said plate further having upper and lower portions of the shape and size to extend beyond the teeth between the gums and the lips, the upper portion being offset forwardly of the lower portion, and a connecting ridge between said upper and lower portions and extending transversely of the plate at least across said frontal section, said offset and ridge forming a bite indentation to accommodate nonocclusion of at least the forward teeth; wherein said improvement comprises wherein said plate is substantially symmetrical in over-all shape, otherwise than said offset and ridge, rendering the same invertible to accommodate nonocclusion of the teeth both in cases of underbite and overbite; said plate further having an inherent curvature also in the direction at right angles to such transverse curvature, imparting to said plate substantially form-sustaining double curvature in the upper and lower portions and in the end portions, said offset and connecting ridge extending along said transverse curvature beyond said frontal section and terminating in said end portions, thereby further rendering said plate from sustaining; and wherein said plate is of substantially transparent, plastic material, said plate further having closure guide line located on said upper and lower portions at least in the frontal section and spaced above and below said ridge at preselected distances, respectively, to indicate optimum jaw closure upon installation, particularly in an edentulous mouth.

An improvement in an expression former for insertion in the mouth of a corpse; said expression former having a marginal shape and size to fit between the lips and the teeth and gums and having an inherent form-sustaining double curvature generally overall, yet being flexible for fitting dental arches of differing curvatures, and further having spurs for engaging and holding the mouth tissues; a bite indentation simulator in said former, comprising upper and lower portions of said former, one of said portions protruding forwardly of the other at least in the region of the forward teeth of said corpse to form an offset along a line extending transversely of the mouth simulating nonocclusion of the teeth, a ridge integrally connecting said upper and lower portions along said offset line; said former having a central portion and an end portion on each side of said central portion: wherein said improvement comprises the medial connecting area being thicker than the wing ends for greater rigidity in the medial connecting area and for greater flexibility in the wing ends.

An improvement in an expression former for insertion in the mouth of a corpse; said expression former having a marginal shape and size to fit between the lips and the teeth and gums and having an inherent form-sustaining double curvature generally overall, yet being flexible for fitting dental arches of differing curvatures, and further having spurs for engaging and holding the mouth tissues; a bite indentation simulator in said former, comprising upper and lower portions of said former, one of said portions protruding forwardly of the other at least in the region of the forward teeth of said corpse to form an offset along a line extending transversely of the mouth simulating nonocclusion of the teeth, a ridge integrally connecting said upper and lower portions along said offset line and comprising: the thickness of the medial connecting area being in the range of 0.011 inches to 0.013 inches; and the thickness of wing ends being in the range of 0.007 inches to 0.009 inches.

An improvement in an expression former for insertion in the mouth of a corpse; said expression former having a marginal shape and size to fit between the lips and the teeth and gums and having an inherent form-sustaining double curvature generally overall, yet being flexible for fitting dental arches of differing curvatures, and further having spurs for engaging and holding the mouth tissues; a bite indentation simulator in said former, comprising upper and lower portions of said former, one of said portions protruding forwardly of the other at least in the region of the forward teeth of said corpse to form an offset along a line extending transversely of the mouth simulating nonocclusion of the teeth, a ridge integrally connecting said upper and lower portions along said offset line; in said central portion a first dividing line and a second dividing line; said first dividing line being in the direction of an adjacent end portion and defining a first flap whose free end is distinct and separate from the central portion; said second dividing line being in the direction of an adjacent end portion and defining a second flap whose free end is distinct and separate from the central portion; the inner part of the first flap connecting with an adjacent end portion; the inner part of the second flap connecting with an adjacent end portion; and said first dividing line and said first flap and said second dividing line and said second flap permitting wider spreading of the expression forming end portions on insertion into the mouth of the corpse and permitting greater adaptation to the dental arch of the corpse.

A method for permitting wider spreading of the end portions of an expression former upon insertion of the expression former into the mouth of a corpse and permitting greater adaptation of the dental former to the arch of the corpse wherein said expression former comprises a thin, flexible plate of resilient, limitedly flexible, yet substantially inelastic material, having an inherent form sustaining double curvature overall to fit the curvature of the dental arch, said plate further having a marginal shape defining a pair of wing ends and a medial connecting area, and a size and shape to extend along the gums beyond the lips at all points, spurs on said plate for engagement with the mouth musculature and wherein said method comprises: forming the medial connecting area to be thicker than the wing ends for greater rigidity in the medial connecting area and for greater flexibility in the wing ends.

A method for permitting wider spreading of the end portions of an expression former upon insertion of the expression former into the mouth of a corpse and permitting greater adaptation of the dental former to the arch of the corpse wherein said expression former comprises a thin, flexible plate of resilient, limitedly flexible, yet substantially inelastic material, having an inherent form sustaining double curvature overall to fit the curvature of the dental arch, said plate further having a marginal shape defining a pair of wing ends and a medial connecting area, and a size and shape to extend along the gums beyond the lips at all points, spurs on said plate for engagement with the mouth musculature and wherein said method comprises: the thickness of the medial connecting area being in the range of 0.011 inches to 0.013 inches; and the thickness of the wing ends being in the range of 0.007 inches to 0.009 inches.

A method for permitting wider spreading of the end portions of an expression former upon insertion of the expression former into the mouth of a corpse and permitting greater adaptation of the dental former to the arch of the corpse wherein said expression former comprises a thin, flexible plate of resilient, limitedly flexible, yet substantially inelastic material, having an inherent form sustaining double curvature overall to fit the curvature of the dental arch, said plate further having a marginal shape defining a pair of wing ends and a medial connecting area, and a size and shape to extend along the gums beyond the lips at all points, spurs on said plate for engagement with the mouth musculature and wherein said method comprises: forming in said frontal section a first dividing line in the direction of an adjacent end portion and defining a first flap whose free end is distinct and separate from the frontal section and whose inner part connects with an adjacent end portion; forming in said frontal section a second dividing line in the direction of an adjacent portion and defining a second flap whose free end is distinct and separate from the frontal section and whose inner part connects with an adjacent end portion; and forming said first dividing line and said second dividing line in opposed direction.

In FIGS. 4 and 5, it is seen that there is a cadaver 56 having an upper lip 58 and a lower lip 60. Also, the cadaver 56 has an upper gum 62 and a lower gum 64.

The cadaver is illustrated in broken line while the frenum lock is in solid line.

The frenum is positioned between the inside of the lips 58 and 60 and outside of the gums 62 and 64.

In FIG. 4, the upper portion 16 of the frenum lock 8 is between the upper lip 58 and the upper gum 62. The lower portion 17 is between the lower lip 60 and the lower gum 64.

In FIG. 5, the frenum lock 8 is positioned so that the lower portion 17 is between the upper lip 58 and the upper gum 62. The upper portion 16 of the frenum lock is between the lower lip 16 and the lower gum 64.

To repeat, screws 30 are positioned in the upper gum 62 and the lower gum 64. Then a wire 32 is attached to the screws and drawn tight so as to close the mouth and to have the gums adjacent or close to each other.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

What I claim is:

1. An improvement in an expression former for insertion between the lips and the teeth and gums of a corpse, comprising a thin plate of resilient, limitedly flexible, yet substantially inelastic material, having an inherent form-sustaining double curvature overall to fit the curvature of the dental arch, said plate further having a marginal shape defining a pair of wing ends and a medial connecting area, and a size and shape to extend along the gums beyond the lips at all points, spurs on said plate for engagement with the mouth musculature, an upper portion offset forwardly of a lower portion thereof at least in the medial area, and a substantially continuous wall connecting said offset portions thereof at least in the medial area, to define a transverse bite indentation ridge therebetween extending along the line of nonocclusion of the forward teeth; and wherein said improvement comprises:

a. the medial connecting area being thicker than the wing ends for greater rigidity in the medial connecting area and for greater flexibility in the wing ends.

2. An improvement according to claim 1 and comprising:

a. the thickness of the medial connecting area being in the range of 0.011 inches to 0.013 inches; and b. the thickness of wing ends being in the range of 0.007 inches to 0.009 inches.

3. An improvement according to claim 1 and comprising:

a. in said medial connecting area a first dividing line and a second dividing line;

b. said first dividing line being in the direction of an adjacent wing end and defining a first flap whose free end is distinct and separate from the medial connecting area;

c. said second dividing line being in the direction of an adjacent wing end and defining a second flap whose free end is distinct and separate from the medial connecting area;

d. the inner part of the first flap connecting with an adjacent wing end;

e. the inner part of the second flap connecting with an adjacent wing end; and f. said first dividing line and said first flap and said second dividing line and said second flap permitting wider spreading of the expression forming wing ends on insertion into the mouth of the corpse and permitting greater adaptation to the dental arch of the corpse.

4. An improvement according to claim 1 and comprising:

a. said first dividing line and said second dividing line being in the upper portion of said medial connecting area.

5. An improvement according to claim 1 and comprising:

a. said first dividing line and said second dividing line being in the lower portion of said medial connecting area.

6. An improvement according to claim 1 and comprising:

a. said first dividing line and said second dividing line being in the upper portion of said medial connecting area;

b. a third dividing line in the lower portion of said medial connecting area and being in the direction of an adjacent wing portion and defining a third flap whose free end is distinct and separate form the medial connecting area;

c. a fourth dividing line in the lower portion of said medial connecting area and being in the direction of an adjacent wing portion and defining a fourth flap whose free end is distinct and separate from the medial connecting area; and d. said third dividing line and said third flap and said fourth dividing line and said fourth flap permitting wider spreading of the expression forming wing ends of insertion into the mouth of the corpse and permitting greater adaptation to the dental arch of the corpse.

7. An improvement according to claim 1 and comprising:

a. the plate is of transparent plastic material and further includes jaw closure guide markings on the medial section of said plate spaced above and below said ridge at distances indicating optimum jaw closure.

8. An improvement according to claim 1 and comprising:

a. the plate is of transparent plastic material and further includes jaw closure guide markings on the medial area of said plate spaced above and below said ridge at distances indicating optimum jaw closure.

9. An improvement in an expression former for insertion in the mouth of a corpse, comprising a thin, flexible plate having spurs thereon for engagement with the mouth musculature, and further having transversely spaced end portions to extend beyond the corners of the mouth and a frontal section connecting said end portions, said plate being of substantially form-retentive material and having an inherent curvature at least transversely of the mouth to fit the curvature of the dental arch, said plate further having upper and lower portions of the shape and size to extend beyond the teeth between the gums and the lips, the upper portion being offset forwardly of the lower portion, and a connecting ridge between said upper and lower portions and extending transversely of the plate at least across said frontal section, said offset and ridge forming a bite indentation to accommodate nonocclusion of at least the forward teeth; wherein said improvement comprises:

a. the medial connecting area being thicker than the wing ends for greater rigidity in the medial connecting area and for greater flexibility in the wing ends.

10. An improvement according to claim 9 and comprising:

a. the thickness of the medial connecting area being in the range of 0.011 inches to 0.013 inches; and b. the thickness of wing ends being in the range of 0.007 inches to 0.009 inches.

11. An improvement according to claim 9 and comprising:

a. in said frontal section a first dividing line and a second dividing line;

b. said first dividing line being in the direction of an adjacent end portion and defining a first flap whose free end is distinct and separate from the frontal section;

c. said second dividing line being in the direction of an adjacent end portion and defining a second flap whose free end is distinct and separate from the frontal section;

d. the inner part of the first flap connecting with an adjacent end portion;

e. the inner part of the second flap connecting with an adjacent end portion; and f. said first dividing line and said first flap and said second dividing line and said second flap permitting wider spreading of the expression forming end portions on insertion into the mouth of the corpse and permitting greater adaptation to the dental arch of the corpse.

12. An improvement according to claim 9 and comprising:

a. wherein said plate is substantially symmetrical in over-all shape, otherwise than said offset and ridge, rendering the same invertible to accommodate nonocclusion of the teeth both in cases of underbite and overbite.

13. An improvement according to claim 9 and comprising:

a. said plate further having an inherent curvature also in the direction at right angles to such transverse curvature, imparting to said plate substantially form-sustaining double curvature in the upper and lower portions and in the end portions, said offset and connecting ridge extending along said transverse curvature beyond said frontal section and terminating in said end portions, thereby further rendering said plate form sustaining.

14. An improvement according to claim 9 and comprising:

a. wherein said plate is of substantially transparent, plastic material, said plate further having closure guide line located on said upper and lower portions at least in the frontal section and spaced above and below said ridge at preselected distances, respectively, to indicate optimum jaw closure upon installation, particularly in an edentulous mouth.

15. An improvement in an expression former for insertion in the mouth of a corpse; said expression former having a marginal shape and size to fit between the lips and the teeth and gums and having an inherent form-sustaining double curvature generally overall, yet being flexible for fitting dental arches of differing curvatures, and further having spurs for engaging and holding the mouth tissues; a bite indentation simulator in said former, comprising upper and lower portions of said former, one of said portions protruding forwardly of the other at least in the region of the forward teeth of said corpse to form an offset along a line extending transversely of the mouth simulating nonocclusion of the teeth, a ridge integrally connecting said upper and lower portions along said offset line; said former having a central portion and an end portion on each side of said central portion: wherein said improvement comprises:

a. the medial connecting area being thicker than the wing ends for greater rigidity in the medial connecting area and for greater flexibility in the wing ends.

16. An improvement according to claim 15 and comprising:

a. the thickness of the medial connecting area being in the range of 0.011 inches to 0.013 inches; and b. the thickness of wing ends being in the range of 0.007 inches to 0.009 inches.

17. An improvement according to claim 15 and comprising:

a. in said central portion a first dividing line and a second dividing line;

b. said first dividing line being in the direction of an adjacent end portion and defining a first flap whose free end is distinct and separate from the central portion;

c. said second dividing line being in the direction of an adjacent end portion and defining a second flap whose free end is distinct and separate from the central portion;

d. the inner part of the first flap connecting with an adjacent end portion;

e. the inner part of the second flap connecting with an adjacent end portion; and f. said first dividing line and said first flap and said second dividing line and said second flap permitting wider spreading of the expression forming end portions on insertion into the mouth of the corpse and permitting greater adaptation to the dental arch of the corpse.

18. A method for permitting wider spreading of the end portions of an expression former upon insertion of the expression former into the mouth of a corpse and permitting greater adaptation of the dental former to the arch of the corpse wherein said expression former comprises a thin, flexible plate of resilient, limitedly flexible, yet substantially inelastic material, having an inherent form sustaining double curvature overall to fit the curvature of the dental arch, said plate further having a marginal shape defining a pair of wing ends and a medial connecting area, and a size and shape to extend along the gums beyond the lips at all points, spurs on said plate for engagement with the mouth musculature and wherein said method comprises:

a. forming the medial connecting area to be thicker than the wing ends for greater rigidity in the medial connecting area and for greater flexibility in the wing ends.

19. A method according to claim 18 and comprising:

a. the thickness of the medial connecting area being in the range of 0.011 inches to 0.013 inches; and b. the thickness of the wing ends being in the range of 0.007 inches to 0.009 inches.

20. A method according to claim 18 and comprising:

a. forming in said frontal section a first dividing line in the direction of an adjacent end portion and defining a first flap whose free end is distinct and separate from the frontal section and whose inner part connects with an adjacent end portion;

b. forming in said frontal section a second dividing line in the direction of an adjacent portion and defining a second flap whose free end is distinct and separate from the frontal section and whose inner part connects with an adjacent end portion; and c. forming said first dividing line and said second dividing line in opposed direction.

21. A combination of a corpse and an improvement in an expression former and comprising:

a. said corpse having lips and gums;

b. said expression former being for insertion between said lips and said gums of said corpse and comprising a thin plate of resilient, limitedly flexible, yet substantially inelastic material, having an inherent form-sustaining double curvature overall to fit the curvature of the dental arch, said plate further having a marginal shape defining a pair of wing ends and a medial connecting area, and a size and shape to extend along the gums beyond the lips at all points, spurs on said plate for engagement with the mouth musculature, an upper portion offset forwardly of a lower portion thereof at least in the medial area, and a substantially continuous wall connecting said offset portions thereof at least in the medial area, to define a transverse bite indentation ridge therebetween extending along the line of nonocclusion of the forward teeth; and wherein said improvement comprises:

c. the medial connecting area being thicker than the wing ends for greater rigidity in the medial connecting area and for greater flexibility in the wing ends.

22. A combination according to claim 21 and comprising:

a. in said medial connecting area a first dividing line and a second dividing line;

b. said first dividing line being in the direction of an adjacent wing end and defining a first flap whose free end is distinct and separate from the medial connecting area;

c. said second dividing line being in the direction of an adjacent wing end and defining a second flap whose free end is distinct and separate from the medial connecting area;

d. the inner part of the first flap connecting with an adjacent wing end;

e. the inner part of the second flap connecting with an adjacent wing end; and f. said first dividing line and said first flap and said second dividing line and said second flap permitting wider spreading of the expression forming wing ends on insertion into the mouth of the corpse and permitting greater adaptation to the dental arch of the corpse.

23. A combination according to claim 21 and comprising:

a. said first dividing line and said second dividing line being in the upper portion of said medial connecting area;

b. a third dividing line in the lower portion of said medial connecting area and being in the direction of an adjacent wing portion and defining a third flap whose free end is distinct and separate form the medial connecting area;

c. a fourth dividing line in the lower portion of said medial connecting area and being in the direction of an adjacent wing portion and defining a fourth flap whose free end is distinct and separate from the medial connecting area; and d. said third dividing line and said third flap and said fourth dividing line and said fourth flap permitting wider spreading of the expression forming wing ends of insertion into the mouth of the corpse and permitting greater adaptation to the dental arch of the corpse.

* * * * *